United States Patent [19]
Venta et al.

[11] Patent Number: 5,816,814
[45] Date of Patent: Oct. 6, 1998

[54] THIRD MOLAR ERUPTION PREDICTOR AND METHOD OF USE

[75] Inventors: Irja Venta, Espoo; Heikki Murtomaa; Pekka Ylipaavalniemi, both of Helsinki, all of Finland

[73] Assignee: Helsinki University Licensing, Ltd., Helsinki, Finland

[21] Appl. No.: 372,041

[22] Filed: Jan. 12, 1995

[51] Int. Cl.⁶ ..................................................... A61C 5/00
[52] U.S. Cl. ............................................. 433/215; 433/72
[58] Field of Search ................................. 433/215, 72, 75, 433/229; 40/661; 33/1 G, 1 BB, 563; 128/777

[56] References Cited

U.S. PATENT DOCUMENTS

| | | | |
|---|---|---|---|
| 1,790,572 | 1/1931 | Bugbee, Jr. | 33/1 BB |
| 2,693,035 | 11/1954 | Beck | 33/563 |
| 3,299,557 | 1/1967 | Schultz | 40/702 |
| 3,878,611 | 4/1975 | Seaman | 433/72 |
| 4,131,998 | 1/1979 | Spears | 33/1 BB |
| 4,738,619 | 4/1988 | Ross | 433/72 |
| 4,884,345 | 12/1989 | Long | 33/1 C |
| 4,986,005 | 1/1991 | Grippi et al. | 33/563 |
| 5,318,441 | 6/1994 | Keller | 433/72 |

FOREIGN PATENT DOCUMENTS

| | | |
|---|---|---|
| 1045464A | 9/1990 | China . |
| 1076603A | 9/1993 | China . |

OTHER PUBLICATIONS

International Search Report; International Application No.: PCT FI 96/00022; International Filing Date, Jan. 10, 1996; Priority Date: Jan. 12, 1995; Applicant: Helsinki University Licensing Ltd OY.

Björk, A, et al., "Mandibular Growth and Third Molar Impaction", *Acta. Odontol. Scand.* 14:231–272 (1956).

Ganss, et al., "Prognosis of third molar eruption," *Oral Surg. Oral Med. Oral Path.*, 76:688–693 (1993).

Habets, et al., "The orthopantomogram, an aid in diagnosis of temporomandibular joint problems. I. The factor of vertical magnification," *Jour. Oral Rehab.* 14:475–480 (1987).

Haavikko, et al., "Predicting Angulational Development and Eruption of the Lower Third Molar," *Angle Orthod.* 48:39–48 (1978).

Henry, et al., "A Preliminary Study of the Eruption of the Mandibular Third Molar Tooth in Man Based on Measurements Obtained from Radiographs with Special Reference to the Problem of Predicting Cases of Ultimate Impaction of the Tooth," *Biometrika* 28:378–427 (1936).

Hugoson, et al., "The Prevalence of Third Molars in a Swedish Population. An Epidemiological Study," *Community Dent. Health* 5:121–138 (1988).

Kaplan, et al., "Some Factors Related to Mandibular Third Molar Impaction," *Angle Orthod.* 45:153–158 (1975).

Olive, et al., "Transverse Dento–Skeletal Relationships and Third Molar Impaction," *Angle Orthod.* 51:41–47 (1981).

Richardson, et al., "The Development of Third Molar Impaction," *Br. J. Orthod.* 2:231–234 (1975).

Richardson, et al., "Longitudinal study of three views of mandibular third molar eruption in males," *Am.J. Orthod.* 86:119–129 (1984).

Ricketts, "Studies Leading to the Practice of Abortion of Lower Third Molars," *Dent.Clin.North Am.* 23: 393–411 (1979).

Sewerin, et al., "A radiographic four–year follow–up study of asymptomatic mandibular third molars in young adults," *Int'l.Dent.J.*, 40:24–30 (1990).

(List continued on next page.)

*Primary Examiner*—Nicholas D. Lucchesi
*Attorney, Agent, or Firm*—Marshall, O'Toole, Gerstein, Murray & Borun

[57] ABSTRACT

Provided are materials and methods for predicting whether a molar tooth will remain impacted or will erupt based upon anatomical measurements of the position of the teeth in relation to the ascending ramus of the mandible.

22 Claims, 7 Drawing Sheets

OTHER PUBLICATIONS

Sewerin, "Praeoperative röntgenunderögelese af 3. molarer i underkaeben omfattende fire projektioner," *Tandlaegebladet* 88:85–90 (1984).

Shiller, et al., "Positional changes in mesio–angular impacted mandibular third molars during a year," *J. Am. Dent. Assoc.* 99:460–464 (1979).

Svendsen, et al., "Prediction of lower third molar impaction from the frontal cephalometric projection," *Eur. J. Orthod.* 7:1–16 (1985).

Ventä, et al., "Clinical follow–up study of third molar eruption from ages 20 to 26 years," *Oral Surg. Oral Med. Oral Path.* 72:150–153 (1991).

Ventä, "Predictive model for impaction of lower third molars," *Oral Sur. Oral Med. Oral Path.*, 76:699–703 (1993).

THIRD MOLAR ERUPTION PREDICTOR AND METHOD OF USE

FIELD OF THE INVENTION

The present invention relates to the field of dentistry and specifically to materials and methods for the prediction of eruption or impaction of molars.

BACKGROUND OF THE INVENTION

The ability to predict the eruption or impaction of molars, and especially third molars, is of considerable value in clinical dentistry because extraction poses a greatly reduced risk to a patient if done when the patient is in his or her twenties as opposed to later in life. However, routine extraction of teeth early in life in order to avoid potential risks of later removal is not considered to be good practice. Means for predicting third molar eruption according to the art are based upon lateral cephalographic measures as reported, for example, in Richardson, et al., *Am. J. Orthod.,* 86: 119–129 (1984). Other early means for predicting eruption include the use of bite-wings, antero-posterior views and periapical films, as reported, for example, in Sewerin, et al., *Int. Dent. J.,* 40: 24–30 (1990). Recently, panoramic tomograms have become more readily available to the practicing dentist as the preferred means for visualizing the mandibular region via X-ray.

There are several reports of measures used to evaluate the clinical status of molar development. These include measurements of the angle of development of the third molar, mesiodistal space available for eruption of the tooth, development of the root, depth of the tooth in bone, and type of impaction. Of the aforementioned measures, the highest probability of predicting eruption (70%) was reported using mesiodistal width as a predictor. Ganss, et al., *Oral Surg. Oral Med. Oral Pathol.,* 76: 688–693 (1993). The highest probability of predicting impaction (94%) was reported by Venta, *Oral Surg. Oral Med. Oral Pathol.,* 76: 699–703 (1993). However, no single method was reported to consistently predict eruption or impaction and methods reported in the art generally involve complicated cephalographic measurements.

The present invention provides a safe, reliable means for predicting the course of development of the lower third molar. Methods and materials according to the invention also eliminate the need for elaborate cephalographic measurements.

SUMMARY OF THE INVENTION

The present invention provides materials and methods for predicting the developmental course of teeth. In particular, materials and methods according to the invention allow one to predict whether a lower third molar (wisdom tooth) will erupt or remain impacted.

In a preferred embodiment of the invention, methods are provided comprising the steps of obtaining an X-ray, and preferably a panoramic tomogram, of a patient's mandibular region; superimposing over said X-ray or panoramic tomogram a sheet, which may be transparent, having a first line and a second line perpendicular to said first line and positioned with respect to the X-ray or tomogram such that said first line is coincident along a superior aspect of an occlusal surface of the first and/or second molars and said second line is tangential to a distal surface of said second molar; and determining a point of intersection of said first line and an anterior border of the ascending ramus of the mandible of said patient.

The distance between the intersection of the first line with the anterior border of the ascending ramus of the mandible and the intersection of the first line with the second line provides a basis for predicting whether the third molar will remain impacted or will erupt. If that distance is 9.5 mm or less, there is an approximately 100% probability that the tooth will remain impacted. If the distance is 16.5 mm or greater, there is an approximately 100% probability that the tooth will erupt.

Also in a preferred embodiment of the invention, the sheet may contain reference points which demarcate critical points (9.5 mm and 16.5 mm) against which intersection of the anterior aspect of the ascending ramus of the mandible with the first line is measured. Using such reference points, the practitioner may visually determine the position of intersection of the ramus with the first line in comparison to the reference points in order to diagnose whether impaction or eruption will take place. For example, if the intersection of the ascending ramus of the mandible and the first line on the sheet is at or mesial to the intersection of a first reference point spaced about 9.5 mm from the intersection of the first and second lines, then it is predicted that the tooth will remain impacted. Similarly, a reference line or point may be drawn at approximately 16.5 mm from the intersection of the first and second lines and eruption may be predicted based upon intersection of the anterior aspect of the ascending ramus of the mandible with the first line at a point at or distal to the 16.5 mm reference point. The reference points are positioned along the first line and may intersect the first line, but it is not necessary that they do so, as the reference points may be lines which terminate above the first line. In the latter case, the reference line may be visually extended to the first line for demarcation of critical areas.

Materials according to the invention comprise a sheet having a first line and a second line perpendicular to a point on the first line. The sheet may optionally include one, two, or three reference points positioned such that a first reference point is spaced about 9.5 mm from the intersection of the first and second lines. A second reference point is positioned approximately 14.5 mm from the intersection of the first and second lines, and a third reference point is positioned at approximately 16.5 mm from the intersection of the first and second lines.

Other aspects and advantages of the invention will become apparent upon consideration of the following detailed description thereof.

DETAILED DESCRIPTION OF THE INVENTION

The present invention provides materials and methods for use in predicting whether a patient's third molar will eventually erupt or remain impacted. Consideration of the methods described herein reveals that such methods may be adapted to the prediction of eruption/impaction of other teeth by simply altering the critical distances on the transparent sheet described herein.

Figure 3:
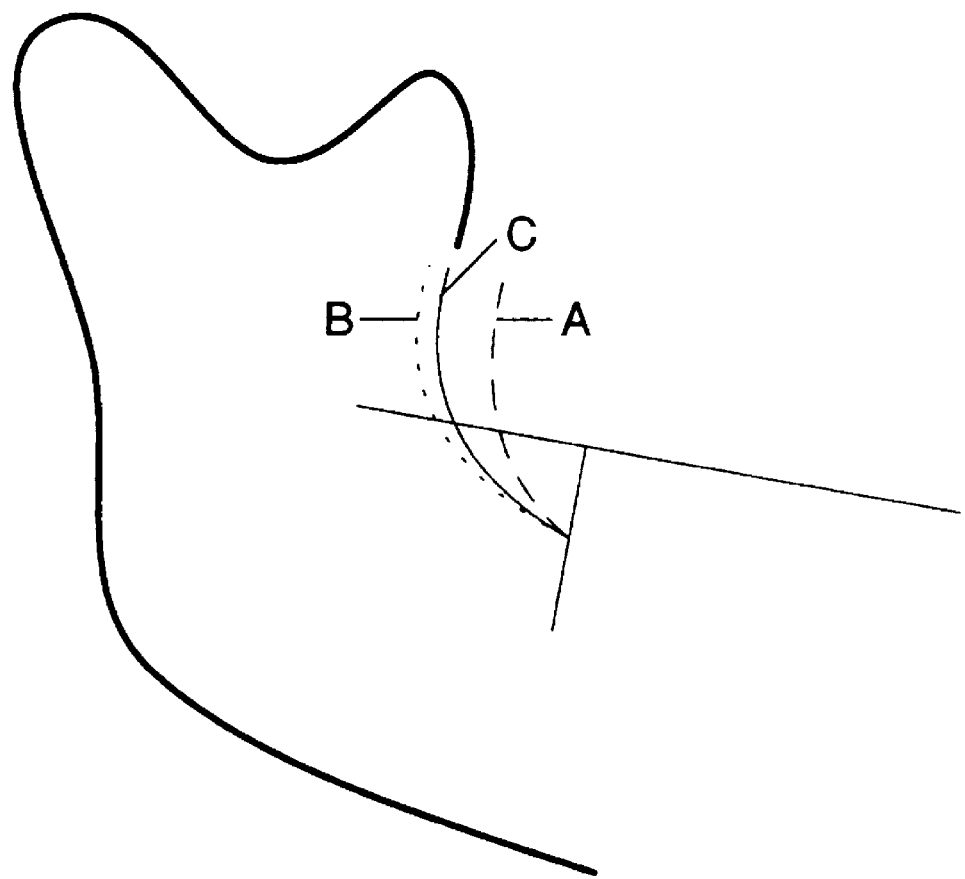
FIG. 3 shows a device for predicting third molar eruption/impaction according to the invention superimposed over a schematic diagram of the mandible.
Figure 4:
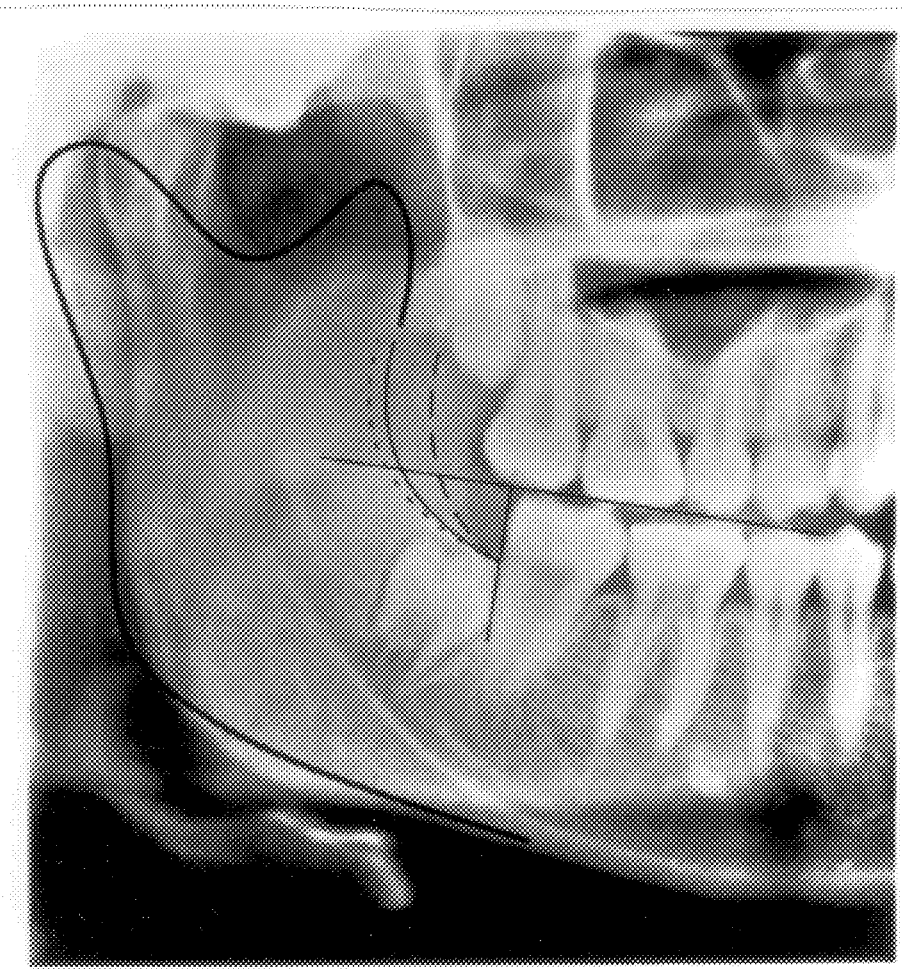
FIG. 4 is a panoramic tomogram with a device according to the invention superimposed thereon.
Figure 5:
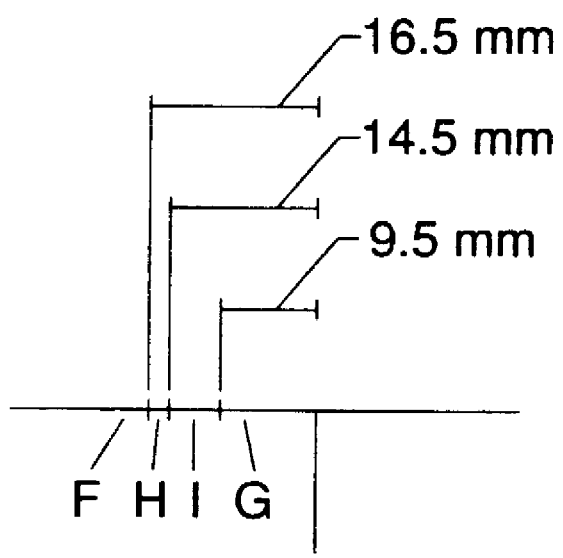
FIG. 5 is a diagram of a device for predicting eruption/impaction according to the invention.

A device according to the invention is shown in FIG. 3 superimposed over a schematic diagram of a mandible. The device is a sheet having thereon a first line and a second line which is perpendicular to the first line, and optionally three reference points. The first reference point, shown as line A in FIG. 3 (long dashes), is positioned along the first line at approximately 9.5 mm from the intersection of the first and second lines. The second reference point, shown as line B in FIG. 3 (short dashes), intersects the first line at a point approximately 16.5 mm from the intersection of the first and second lines. A third reference point, shown as line C in FIG. 3 (solid line between the two broken lines) represents the cut-off point for predicting eruption/impaction. Only the intersections of the various reference lines with the first line are important for purposes of the invention. Thus, it is immaterial whether the reference lines are curved. If the intersection of the first line with the anterior aspect of the ascending ramus of the mandible is mesial to the solid reference line, continued impaction is predicted at a probability of about 76%; whereas if the intersection of the first line with the anterior aspect of the ascending ramus of the mandible is distal to the solid reference line then eruption is predicted at a probability of about 72%. FIG. 4 represents a device according to the invention superimposed upon a tomogram showing an ascending ramus of the mandible. FIG. 5 shows a diagram of a device according to the invention with reference points at 9.5 mm, 14.5 mm, and 16.5 mm. The only critical position is the point of intersection with the first line of the device.

Figure 6:
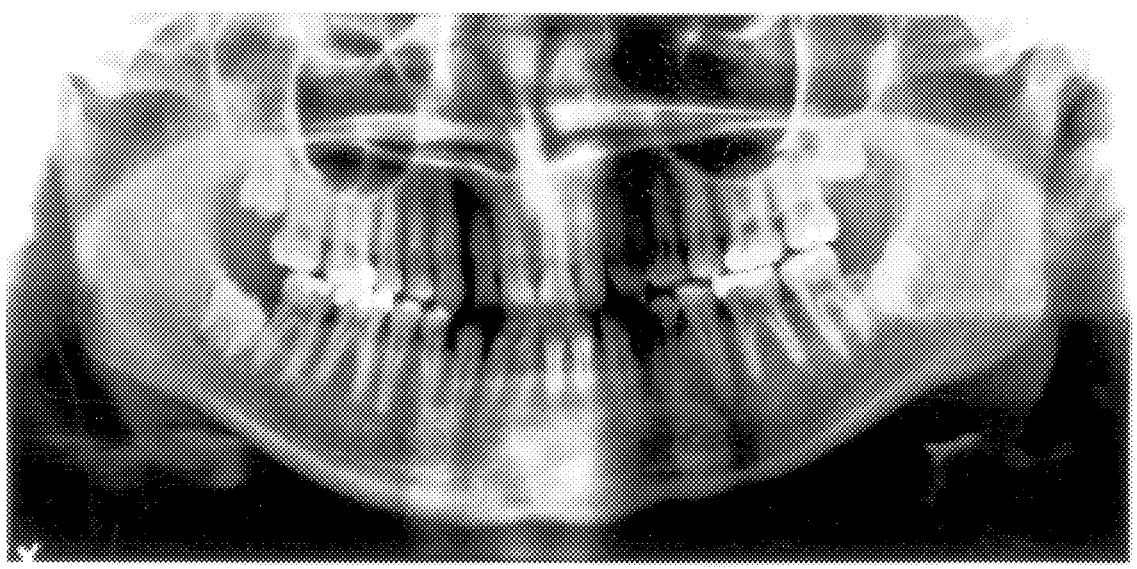
FIG. 6 is a copy of a panoramic tomogram showing a lower third molar predicted by the invention to erupt.
Figure 7:
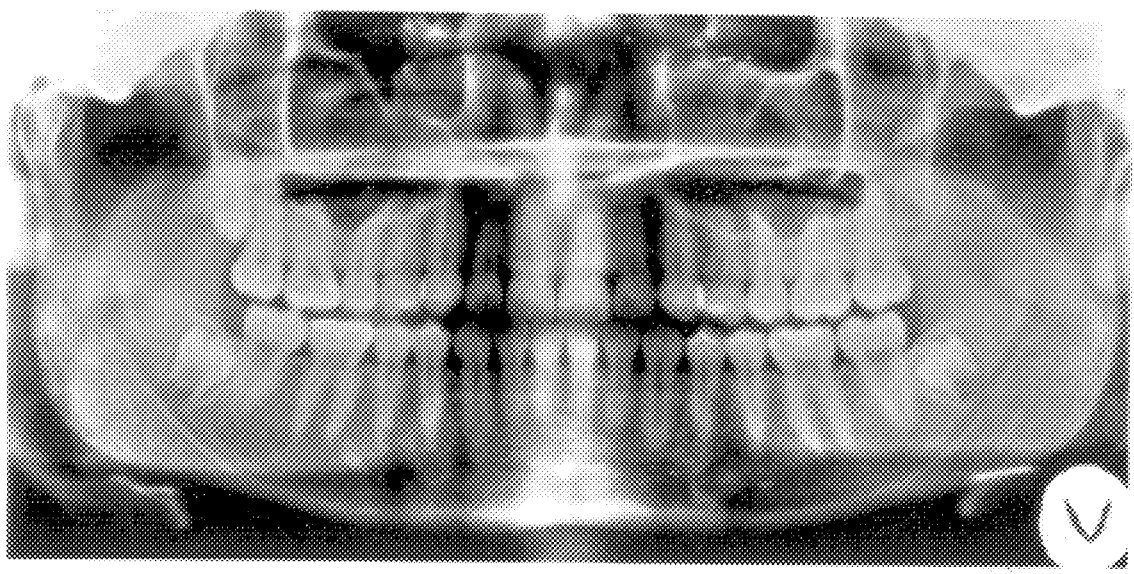
FIG. 7 is a copy of a panoramic tomogram showing a lower third molar predicted by the invention to remain impacted.

The device shown in FIGS. 3, 4, and 5 is superimposed over a panoramic tomogram of the mandibular region, including the region of the molars. The device is placed on the tomogram such that the first line coincides with the superior (occlusal) surface of the first and second molars and the second, perpendicular line coincides with the distal surface of the second molar. FIG. 4 shows proper placement of the device over a tomogram or X-ray. Upon placement over the tomogram, the clinician may either measure the distance from the point of intersection of the first and second lines to the anterior aspect of the ascending ramus or the aforementioned reference points may be used to predict the developmental fate of the lower third molar. Intersection of the first line with the anterior aspect of the ascending ramus mesial to line A in FIG. 3 constitutes an approximately 100% probability that the third molar will remain impacted. Intersection distal to line B in FIG. 3 results in an approximately 100% probability of eruption of the third molar. Intersection between lines A and C in FIG. 3 results in a high probability of continued impaction and intersection between lines C and B indicates a high probability of eruption as discussed below. FIGS. 6 and 7 are panoramic tomograms which show lower third molars predicted to erupt and to be impacted, respectively, according to the invention.

The result of the invention is that the practitioner may advise patients whether to seek removal of the third molar at an age where such surgery is relatively less risky as compared to performing the surgery at a later age. Accordingly, use of claimed materials and methods on individuals in their late teens or early twenties is preferred.

The following example provides details of the development of the invention and some of its preferred applications.

EXAMPLE

A longitudinal study was carried out at the Finnish Student Health Service by the University of Helsinki. Subjects were 40 University students (25% male, 75% female) who were evaluated during a six-year period from age 20 through age 26. All subjects had non-erupted third molars at the beginning of the study. Panoramic tomograms were taken of all subjects and the clinical status of the third molars of all subjects was recorded (i.e. orientation, etc.). Tomograms were taken with an Orthopantomograph™ OP-3 SE (Palomex, Instru, Finland) and with a Cranex™ DC SL-4 (Soredex, Orion Corp., Espoo, Finland).

Tomograms were analyzed using a transparent overlay (the device) according to the invention which was labeled as shown in FIG. 3. The overlay was placed directly on each tomogram such that the first line on the overlay lay directly over the occlusal (superior) aspect of the first and second molars. As the superior surface of the first and second molars is not always a straight line, one must match the first line on the overlay to the superior surface to the best extent possible. The second line on the overlay was lined up with the posterior surface of the second molar. An example of the manner in which the transparency was placed on a tomogram is shown in FIG. 4.

Figure 1:
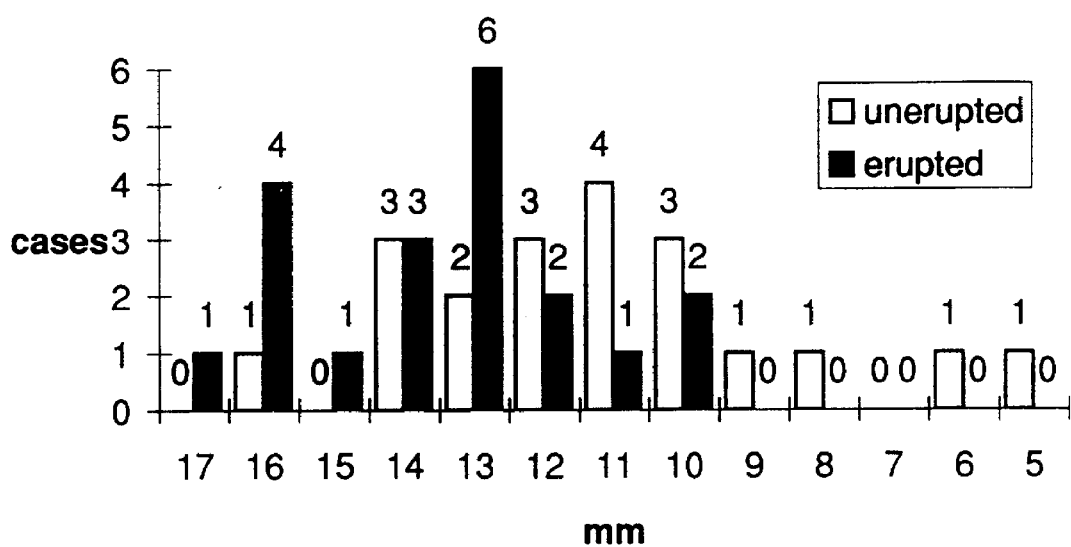
FIG. 1 is a histogram showing distances to the intersection of the first line and the anterior aspect of the ascending ramus in patients with finally erupted or impacted third molars.

Distances from the intersection of the first and second lines and the anterior border of the ascending ramus of the mandible were measured for each patient. Results are presented in FIG. 1 which is a histogram showing the distances for patients whose third molars were finally erupted six years after initial measurement (dark boxes) and those for patients whose third molars remained impacted six years after initial measurement (light boxes). Although clear distinctions exist between finally erupted teeth and finally impacted teeth in terms of the above-noted measurement, Bayes' Decision Theory was used to determine a cutoff for purposes of predicting whether a tooth would ultimately erupt or remain impacted. According to Bayes' Decision Theory, the sum of false negatives (beta error) and false positives (alpha error) is at a minimum when two distribution curves intersect. For the data shown in FIG. 1, the sum of the alpha error and beta error was lowest at a distance of 12.5 mm distal to the point of intersection of the first and second lines (i.e., the distal surface of the second molar).

Figure 2:
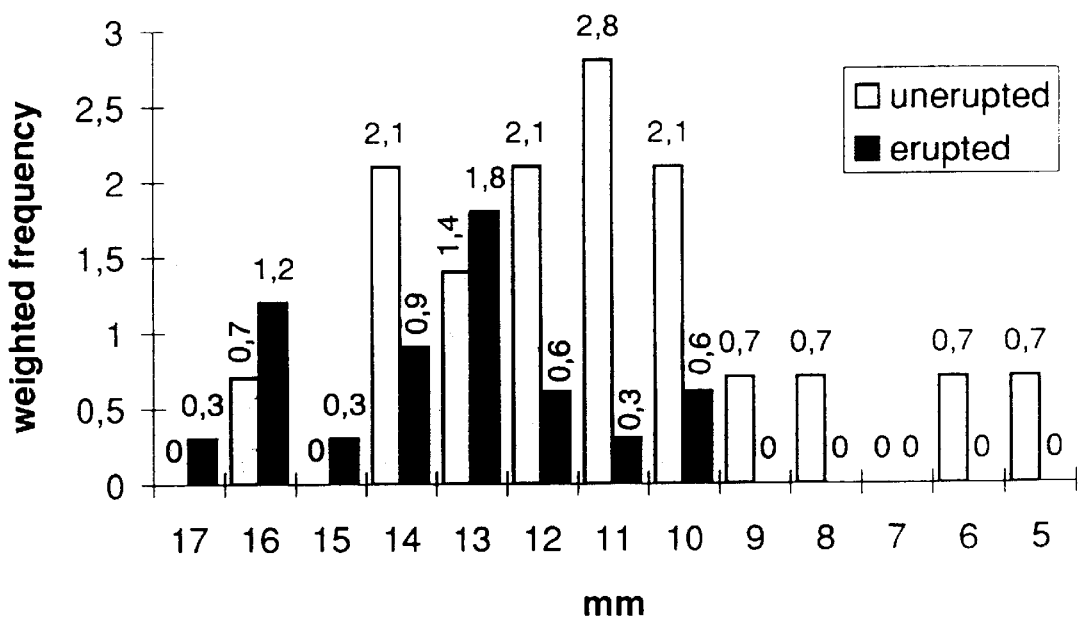
FIG. 2 is a weighted histogram showing distances to the intersection of the first line and the anterior aspect of the ascending ramus in patients with finally erupted or impacted third molars.

A priori probabilities for eruption and impaction of lower third molars are 30% and 70%, respectively. Because impaction is more common than eruption, the cutoff for predicting impaction or eruption may be more distal from the distal surface of the second molar than would be predicted by straightforward probability analysis. Accordingly, a weighted decision point may be obtained, as shown in FIG. 2, by weighing the values in FIG. 1 by their respective a priori probabilities (30% and 70%). When this is done, a new cutoff point is generated 14.5 mm from the point of intersection of the first and second lines based upon the fact that the sum of false negatives and false positives in the weighted histogram of FIG. 2 is lowest at a point 14.5 mm from the distal surface of the second molar as shown below in Table 1.

TABLE 1

Variables calculated from weighted histograms (in percent).

|  | 13.5 mm | 14.5 mm | 15.5 mm |
|---|---|---|---|
| False negatives + false positives | 31 | 25 | 26 |
| Sensitivity | 80 | 95 | 95 |
| Specificity | 45 | 30 | 25 |
| Probability of eruption | 49 | 72 | 68 |
| Probability of impaction | 77 | 76 | 75 |

From the above data, lines were established on the transparent sheet which intersect the first line at 9.5, 14.5 and 16.5 mm, respectively (Lines A, C, and B, respectively, in FIG. 3). Those lines were used to predict eruption/impaction in test subjects. Twenty test subjects were given panoramic tomograms at a mean age of 20.7 years (s.d. 0.6) and again at 25.3 years (s.d. 0.7) and the device described above and shown in FIG. 3 was used to predict eruption or impaction based upon the point at which the first line of the device intersects the anterior surface of the patient's ascending mandibular ramus. Significant differences between sample means related to mesiodistal space available were found using the t-test with a pooled variance estimate.

The device shown in FIG. 3 was applied to each tomogram as a transparent sheet superimposed upon the tomogram, wherein the cutoff point (line C in FIG. 3) for predicting eruption/impaction was 14.5 mm. If the first line intersects the anterior aspect of the ascending ramus of the mandible at or mesial to a distance of 9.5 mm (line A in FIG. 3) there was a 100% probability that the tooth would remain impacted. If the intersection of the first line and the anterior aspect of the ascending ramus was distal to 16.5 mm from the second line there was a 100% probability of eruption. If the intersection of the first line and the anterior border of the ascending ramus is between Lines A and C in FIG. 3, there is a greater probability of impaction; whereas if that intersection is at a point between Lines C and B in FIG. 3, there is a greater probability of eruption. The relevant predictors are shown in FIG. 5. If the intersection between the first line and the anterior border of the ascending ramus occurs in the area marked "F", eruption is predicted to occur 100% of the time. If that intersection occurs in the area marked "G", impaction is predicted to occur 100% of the time. If the intersection is in the area marked "H", eruption is more likely than impaction; whereas if the intersection occurs in the area marked "I", impaction is more likely than eruption.

Results indicated that the difference in mean mesiodistal crown width of lower third molars which remained impacted and those which erupted was not significant (15.4 mm and 15.1, respectively). However, the mean values of the distance from the intersection of the first and second (perpendicular) lines to the anterior aspect of the ascending ramus were 11.1 mm (s.d. 2.7) for impacted third molars and 13.6 mm (s.d. 2.0) for erupted third molars. The difference in those values was statistically significant (p<0.01). Accordingly, there is significantly more mesiodistal space in the retromolar area when third molars erupted as opposed to when they remained impacted. In fact, use of the device shown in FIG. 3 resulted in 97% predictability in the longitudinal study referred to above. Only one exceptionally small tooth in a male patient in the study failed to meet the predicted outcome (the tooth erupted when use of the device predicted impaction).

The present invention has been described in terms of its preferred embodiments and further aspects of the invention are apparent to skilled artisan based upon knowledge in the art in light of the present disclosure.

We claim:

1. A device for predicting eruption of third molars, comprising:

a sheet; and means disposed on said sheet for predicting eruption of third molars when superimposed on an x-ray, said means comprising an indicium denoting a first axis and an indicium denoting a second axis perpendicular to said first axis, with means associated with the indicium denoting said first axis identifying a reference point positioned and spaced about 14.5 mm from a point of intersection of said first and second axes.

2. The device of claim 1, further comprising means associated with the indicium denoting said first axis identifying a second reference point positioned and spaced about 9.5 mm from said point of intersection of said first and second axes.

3. The device of claim 2, further comprising means associated with the indicium denoting said first axis identifying a third reference point positioned and spaced about 16.5 mm from said point of intersection of said first and second axes.

4. The device of claim 1, further comprising means associated with the indicium denoting said first axis identifying another reference point positioned and spaced about 16.5 mm from said point of intersection of said first and second axes.

5. The device of claim 1, wherein said sheet is transparent.

6. A The device of claim 1, wherein said indicia denoting said first and second axes are lines.

7. The device of claim 6, wherein said lines are solid lines.

8. The device of claim 1, wherein said means identifying said reference point is a line passing through said reference point.

9. The device of claim 8, wherein said line is a solid line.

10. A device for predicting eruption of third molars, comprising.

a sheet; and means disposed on said sheet for predicting eruption of third molars when superimposed on an x-ray, said means comprising an indicium denoting a first axis and an indicium denoting a second axis perpendicular to said first axis, with means associated with the indicium denoting said first axis identifying a reference point positioned and spaced about 16.5 mm from a point of intersection of said first and second axes.

11. The device of claim 10, further comprising means associated with the indicium denoting said first axis identifying a second reference point positioned and spaced about 9.5 mm from said point of intersection of said first and second axes.

12. A device for predicting eruption of third molars, comprising:

a sheet; and means disposed on said sheet for predicting eruption of third molars when superimposed on an x-ray, said means comprising an indicium denoting a first axis and an indicium denoting a second axis perpendicular to said first axis, with means associated with the indicium denoting said first axis identifying a reference point spaced about 9.5 mm from a point of intersection of said first and second axes.

13. A method for predicting eruption of third molars in a patient, comprising the steps of:

obtaining an x-ray image of said patient's mandibular region;

superimposing over said x-ray a sheet, said sheet having an indicium denoting a first axis and an indicium denoting a second axis perpendicular to said first axis and means associated with said indicium denoting said first axis identifying a reference point, such that said indicium denoting said first axis is coincident with a plane defined by a superior aspect of a first and a second molar and said indicium denoting said second axis is tangential to a distal surface of said second molar;

determining a point of intersection of said first axis and an anterior border of the proximal ascending ramus of the mandible of said patient;

measuring the distance from said point of intersection of said first axis and said anterior border of said ramus to a point of intersection of said first and second axes on said sheet; and comparing said distance between the point of intersection of the first axis and said anterior border of the ascending ramus with said means identifying said reference point on said sheet.

14. The method of claim 13, wherein the superimposing step further comprises said sheet having means identifying said reference point positioned and spaced about 14.5 mm from a point of intersection of said first and second axes.

15. The method of claim 14, wherein said sheet further comprises having a means identifying a second reference point positioned and spaced about 9.5 mm from said point of intersection of said first and second axes.

16. The method of claim 15, wherein said sheet further comprises having a means identifying a third reference point positioned and spaced about 16.5 mm from said point of intersection of said first and second axes.

17. The method of claim 13, wherein the superimposing step further comprises said sheet having means identifying said reference point positioned and spaced about 16.5 mm from a point of intersection of said first and second axes.

18. The method of claim 17, wherein said sheet further comprises having a means identifying a second reference point positioned and spaced about 14.5 mm from said point of intersection of said first and second axes.

19. The method of claim 17, wherein said sheet further comprises having a means identifying a second reference point positioned and spaced about 9.5 mm from said point of intersection of said first and second axes.

20. The method of claim 13, wherein the superimposing step further comprises said sheet having means identifying said reference point positioned and spaced about 9.5 mm from a point of intersection of said first and second axes.

21. The method of claim 13, wherein said sheet is transparent.

22. The method of claim 13, wherein said x-ray image is a panoramic tomogram.

* * * * *

UNITED STATES PATENT AND TRADEMARK OFFICE
CERTIFICATE OF CORRECTION

PATENT NO. : 5,816,814
DATED : October 6, 1998
INVENTOR(S) : Venta et al.

It is certified that error appears in the above-identified patent and that said Letters Patent is hereby corrected as shown below:

At Column 6, line 33, delete "A" at the beginning of the claim.

Signed and Sealed this

Ninth Day of May, 2000

*Attest:*

Q. TODD DICKINSON

*Attesting Officer*     *Director of Patents and Trademarks*